United States Patent
Sinha et al.

(10) Patent No.: US 8,383,646 B2
(45) Date of Patent: Feb. 26, 2013

(54) THERAPEUTIC ((BICYLICHETEROARYL)IMIDAZOLYL) METHYLHETEROARYL COMPOUNDS

(75) Inventors: Santosh C. Sinha, Ladera Ranch, CA (US); Todd M. Heidelbaugh, Fountain Valley, CA (US); Ken Chow, Newport Coast, CA (US); Smita S. Bhat, Irvine, CA (US); Phong X. Nguyen, Placentia, CA (US); Michael E. Garst, Neport Beach, CA (US)

(73) Assignee: Allergan, Inc., Irvine, CA (US)

( * ) Notice: Subject to any disclaimer, the term of this patent is extended or adjusted under 35 U.S.C. 154(b) by 107 days.

(21) Appl. No.: 12/600,757

(22) PCT Filed: May 21, 2008

(86) PCT No.: PCT/US2008/064284
§ 371 (c)(1),
(2), (4) Date: Mar. 22, 2010

(87) PCT Pub. No.: WO2008/147786
PCT Pub. Date: Dec. 4, 2008

(65) Prior Publication Data
US 2010/0190823 A1  Jul. 29, 2010

Related U.S. Application Data

(60) Provisional application No. 60/939,773, filed on May 23, 2007.

(51) Int. Cl.
*A61K 31/47* (2006.01)
*C07D 401/14* (2006.01)

(52) U.S. Cl. ........ 514/314; 546/112; 546/152; 546/181; 514/299; 514/311

(58) Field of Classification Search ............. 546/112, 546/152, 181; 514/299, 311, 314
See application file for complete search history.

(56) References Cited

U.S. PATENT DOCUMENTS

| 6,258,824 | B1 * | 7/2001 | Yang | 514/312 |
|---|---|---|---|---|
| 7,141,597 | B2 | 11/2006 | Chow et al. | |
| 7,902,247 | B2 * | 3/2011 | Sinha et al. | 514/396 |
| 8,124,774 | B2 * | 2/2012 | Sinha et al. | 546/159 |

FOREIGN PATENT DOCUMENTS

| GB | 2101114 A | 7/1981 |
|---|---|---|
| WO | WO 92/00073 | 1/1992 |

OTHER PUBLICATIONS

Richard B. Silverman "Prodrugs and Drug Delivery Systems,", Organic Chemistry of Drug Design and Drug Action, 2d Ed., Elsevier Academic Press: Amsterdam, 2004, pp. 496-557.
Messier et al., Pharmacol Toxicol, 76, pp. 308-311; 1995.
Robert R. Ruffolo, Jr., α-Adrenoreceptors: Molecular Biology, Biochemistry and Pharmacology, (Progress in Basic and Clinical Pharmacology series, Karger, 1991).

* cited by examiner

*Primary Examiner* — Golam M M Shameem
(74) *Attorney, Agent, or Firm* — Kevin J. Forrestal

(57) ABSTRACT

Disclosed herein is a compound of the formula (I) therapeutic methods, compositions, and medicaments related thereto are also disclosed.

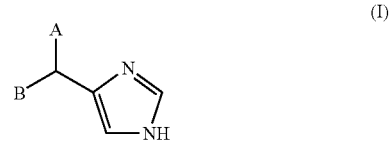

(I)

16 Claims, No Drawings

THERAPEUTIC ((BICYLICHETEROARYL)IMIDAZOLYL) METHYLHETEROARYL COMPOUNDS

CROSS REFERENCE

This is a national stage application under 35 U.S.C. §371 of PCT patent application PCT/US08/64284, filed on May 21, 2008, which claims the benefit of U.S. Provisional Patent Application U.S. application Ser. No. 60/939,781, filed May 23, 2007, each of which is hereby incorporated by reference in its entirety.

BACKGROUND

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction). For a further general background on the $\alpha$-adrenergic receptors, the reader's attention is directed to Robert R. Ruffolo, Jr., $\alpha$-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting a-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$ and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha$_2$ adrenergic receptor agonist activity are known analgesics. However, many compounds having such activity do not provide the activity and specificity desirable when treating disorders modulated by alpha$_2$ adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

DESCRIPTION OF THE INVENTION

Disclosed herein is a compound of the formula

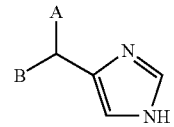

wherein A is monocyclic heteroaryl having 0, 1, 2, or 3 substituents; and B is a fused ring system consisting of:
  a phenyl ring which attaches to the remainder of the molecule,
  a second heterocyclic five-, or six-membered ring which is fused to the phenyl ring,
  and 0, 1, 2, or 3 substituents which attach to one or both of the phenyl ring and the second ring;
wherein each substituent independently consists of from 0 to 8 carbon atoms, from 0 to 3 oxygen atoms, from 0 to 3 halogen atoms, from 0 to 2 nitrogen atoms, from 0 to 2 sulfur atoms, and from 0 to 24 hydrogen atoms.

Unless otherwise indicated, reference to a compound should be construed broadly to include pharmaceutically acceptable salts, prodrugs, tautomers, alternate solid forms, and non-covalent complexes of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt is an association of an ionic form of the compound, such as a conjugate acid or base, with a corresponding amount of counter-ions. Salts can form from or incorporate one or more deprotonated acidic groups, one or more protonated basic groups (e.g. amines), or both (e.g. zwitterions).

A prodrug is a compound which is converted to a therapeutically active compound after administration. While not intending to limit the scope of the invention, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. They often, but do not necessarily, include a transfer of a proton, hydrogen atom, or hydride ion. For example, the structures herein are intended to include, but are not limited to, the tautomeric forms shown below.

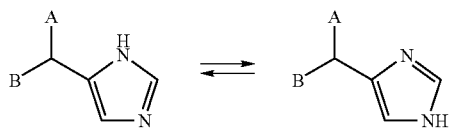

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

A is monocyclic heteroaryl, meaning an aromatic ring with one or more nitrogen, sulfur, or oxygen atoms in the ring. Typical examples of heteroaryl include pyridyl, thienyl, furyl, pyrrolyl, pyrrolidinyl, imidazolyl, oxazolyl, thiazolyl, pyrazolyl, pyrimidinyl, and pyrazinyl. A can be unsubstituted, or substituted with up to 3 substituents.

B is a fused ring system consisting of: a phenyl ring which attaches to the remainder of the molecule, a second heterocyclic five-, or six-membered ring which is fused to the phenyl ring, and 0, 1, 2, or 3 substituents which attach to one or both of the phenyl ring and the second ring.

In other words, structures such as the ones shown below are contemplated. Bond "a" connects the phenyl ring of B to the rest of the molecule. The second heterocyclic five-, or six membered ring fused to the phenyl ring is represented by Z. Finally, $R^1$, $R^2$, and $R^3$ represent hydrogen atoms or substituents subject to the constraints given herein.

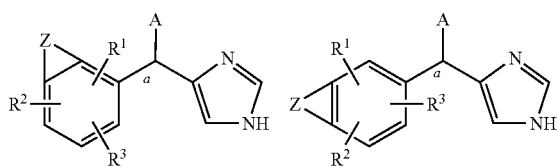

The heterocyclic five- or six-membered ring has at least one nitrogen, sulfur, or oxygen atom in the ring. It can be heteroaromatic or non-aromatic. The substituents may be attached to the phenyl ring, the heteroaromatic ring, or substituents may be attached to both rings.

Typical examples of B include: quinolinyl, quinoxalinyl, indolyl, benzothienyl, benzofuryl, benzofuranyl, benzodioxolyl, 2,3-dihydrobenzo[b][1,4]dioxin-6-yl, and the like.

Quinolinyl includes isoquinolinyl and other isomers, such as the structures shown below, either unsubstituted as depicted or having substituents subject to the constraints herein.

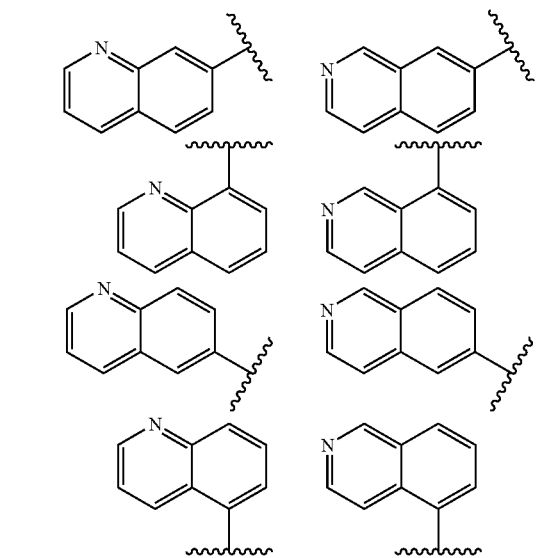

The substituents of A and B are subject to the same constraints. However, the substituents are independent, meaning that A and B may have the same or different substituents; the substituents on A may be the same or different from one another; and the substituents on B may be the same or different from one another.

Subject to the constraints described herein (e.g. limits on the number of atoms for a substituent), examples of substituents include, but are not limited to:

Hydrocarbyl, meaning a moiety consisting of carbon and hydrogen only, including, but not limited to:
  a. alkyl, meaning hydrocarbyl having no double or triple bonds, including, but not limited to:
     linear alkyl, e.g. methyl, ethyl, n-propyl, n-butyl, n-pentyl, n-hexyl, etc.,
     branched alkyl, e.g. iso-propyl, t-butyl and other branched butyl isomers, branched pentyl isomers, etc.,
     cycloalkyl, e.g. cyclopropyl, cyclobutyl, cyclopentyl, cyclohexyl, etc.,
     combinations of linear, branched, and/or cycloalkyl;
  b. alkenyl, e.g. hydrocarbyl having 1 or more double bonds, including linear, branched, or cycloalkenyl
  c. alkynyl, e.g. hydrocarbyl having 1 or more triple bonds, including linear, branched, or cycloalkenyl;
  d. combinations of alkyl, alkenyl, and/or akynyl
  alkyl-CN, such as —$CH_2$—CN, —$(CH_2)_2$—CN; —$(CH_2)_3$—CN, and the like;
  hydroxyalkyl, i.e. alkyl-OH, such as hydroxymethyl, hydroxyethyl, and the like;
  ether substituents, including —O-alkyl, alkyl-O-alkyl, and the like;
  thioether substituents, including —S-alkyl, alkyl-S-alkyl, and the like;
  amine substituents, including —$NH_2$, —NH-alkyl, —N-$alkyl^1 alkyl^2$ (i.e., $alkyl^1$ and $alkyl^2$ are the same or different, and both are attached to N), alkyl-$NH_2$, alkyl-NH-alkyl, alkyl-N-$alkyl^1 alkyl^2$, and the like;
  aminoalkyl, meaning alkyl-amine, such as aminomethyl (—$CH_2$-amine), aminoethyl, and the like;
  ester substituents, including —$CO_2$-alkyl, —$CO_2$-phenyl, etc.;

other carbonyl substituents, including aldehydes; ketones, such as acyl (i.e.

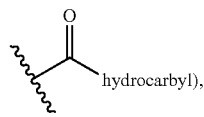

and the like; in particular, acetyl, propionyl, and benzoyl substituents are contemplated;

phenyl or substituted phenyl;

fluorocarbons or hydroflourocarbons such as —$CF_3$,-$CH_2CF_3$, etc.; and

—CN;

combinations of the above are also possible, subject to the constraints defined;

Alternatively, a substituent may be —F, —Cl, —Br, or —I.

In particular, alkyl having from 1 to 8 carbon atoms is contemplated as a substituent.

Alternatively, alkyl having from 1 to 4 carbon atoms is contemplated;

Substituents must be sufficiently stable to be stored in a bottle at room temperature under a normal atmosphere for at least 12 hours, or stable enough to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of heavy atoms in a substituent. Thus, for example, the salt —$CO_2^-Na^-$ is a stable substituent consisting of 3 heavy atoms, i.e. sodium is not counted. In another example, the salt —$NH(Me)_2^+Cl^-$ is a stable substituent consisting of 3 heavy atoms, i.e. chlorine is not counted.

In one embodiment, A is pyridinyl, meaning that compounds of structures such as those shown below are contemplated.

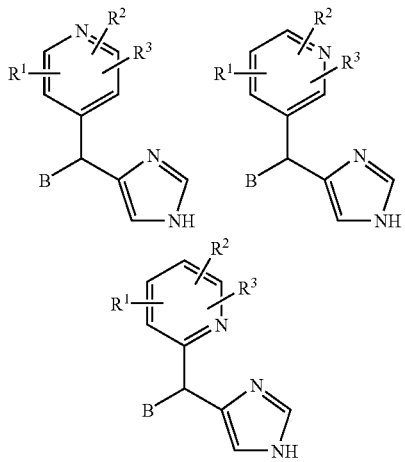

In these structures, $R^1$, $R^2$, and $R^3$ are substituents as defined herein.

In another embodiment, A is thienyl, meaning that compounds of structures such as those shown below are contemplated.

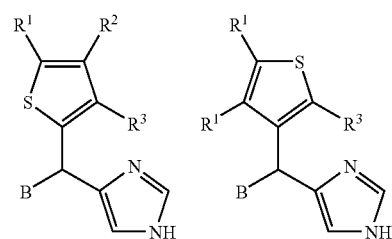

In these structures, $R^1$, $R^2$, and $R^3$ are substituents as defined herein.

In another embodiment, A is furyl, meaning that compounds of structures such as those shown below are contemplated.

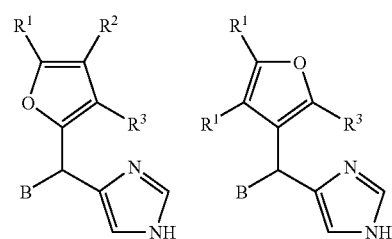

In these structures, $R^1$, $R^2$, and $R^3$ are hydrogen or substituents, as defined herein.

In one embodiment, A is pyridinyl, thienyl, furyl, or pyrrolyl.

In another embodiment, each substituent is independently —H, alkyl having from 1 to 8 carbon atoms, —F, —Cl, —Br, —$CH_2OH$, an amine having from 0 to 8 carbon atoms, —$CH_2CN$, —$CF_3$, or acyl having from 1 to 8 carbons.

In another embodiment, A is pyridinyl.

In another embodiment, B is quinolinyl.

In another embodiment each substituent of B is —H, —F, —Cl, —Br, —$CH_3$, —$NHCH_3$, or —$CF_3$.

Hypothetical examples of useful compounds include those shown below.

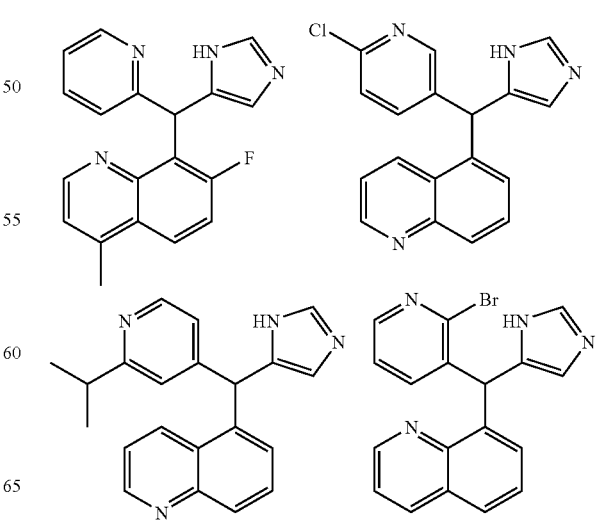

-continued
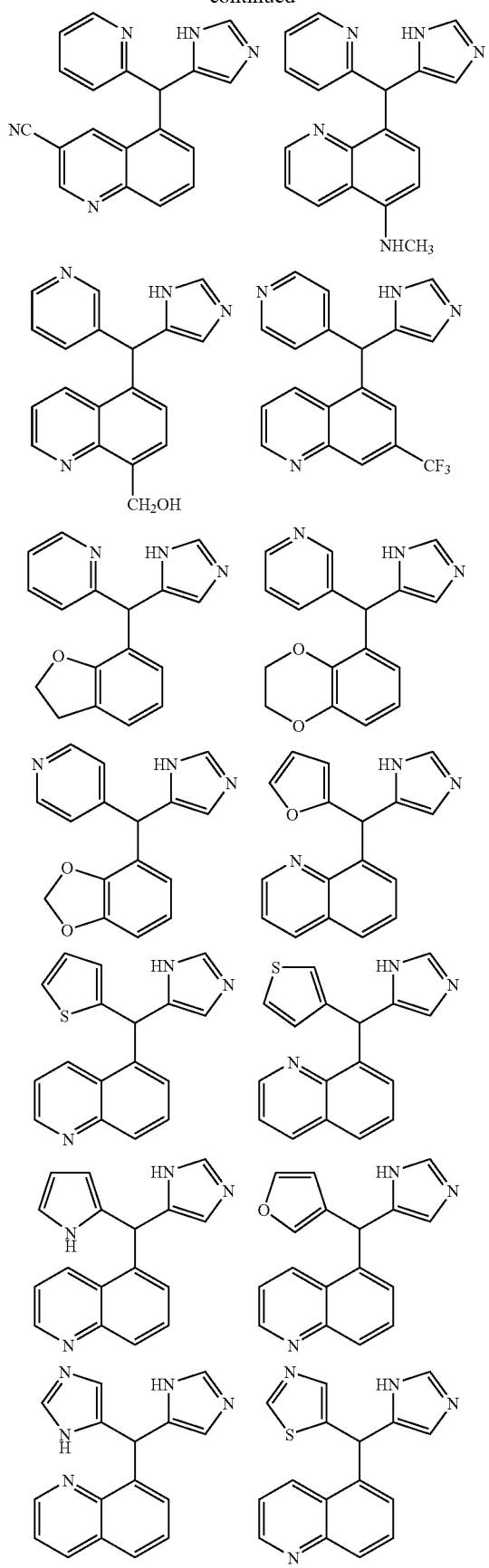
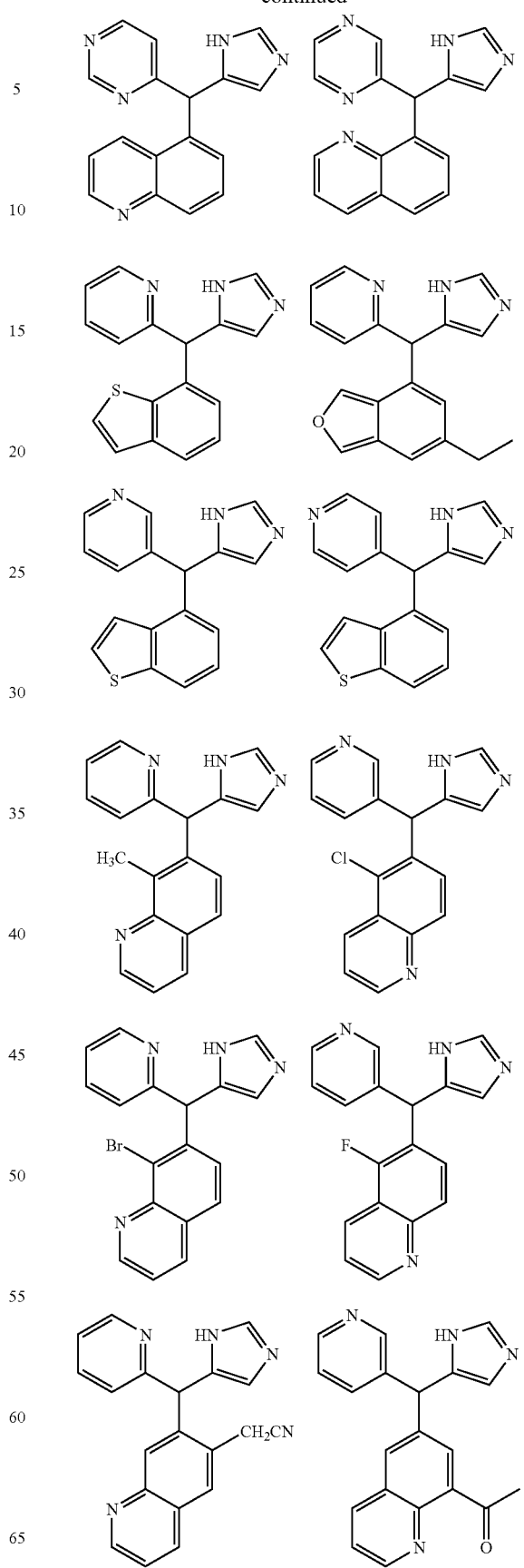

-continued
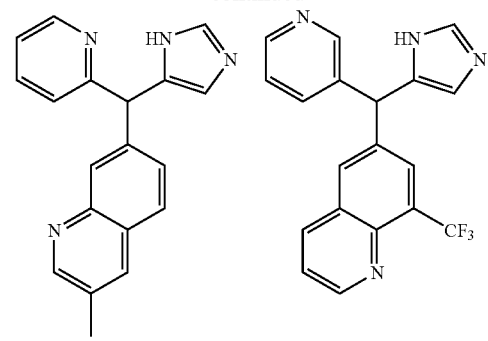
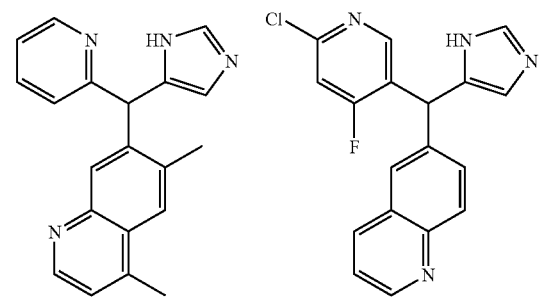
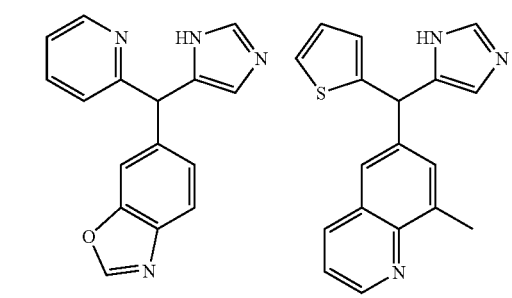
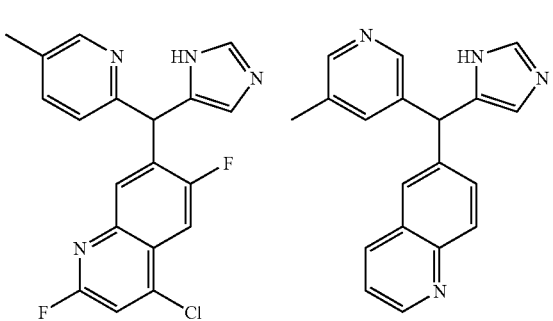
-continued
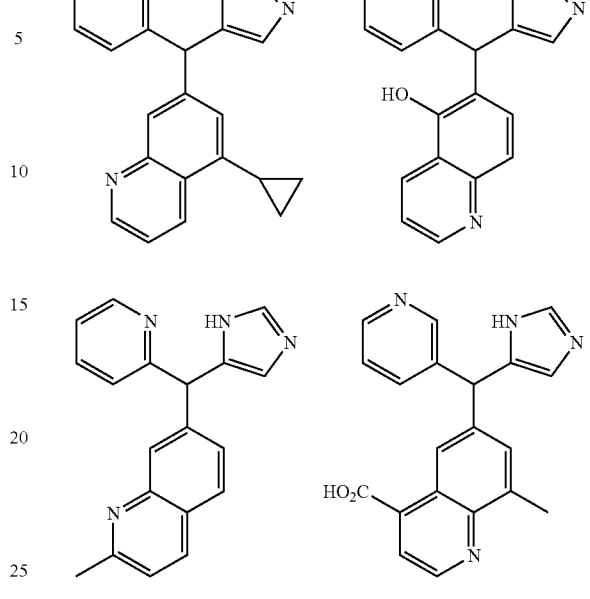
Synthetic Methods
Method A: Procedure for the preparation of 8-((1H-imidazol-5-yl)(pyridin-2-yl)methyl)quinoline (301)
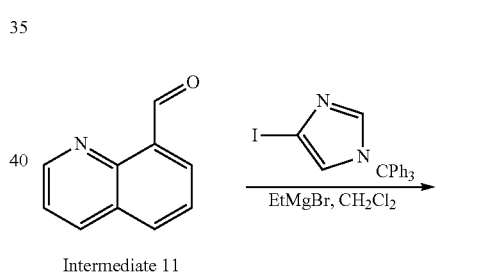
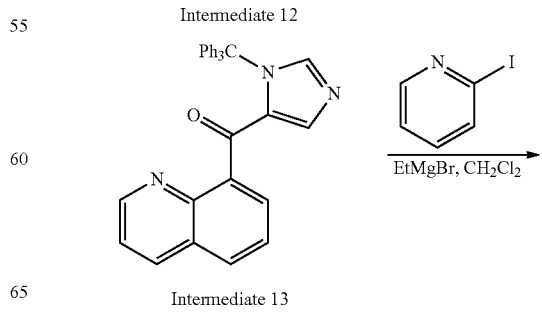

-continued

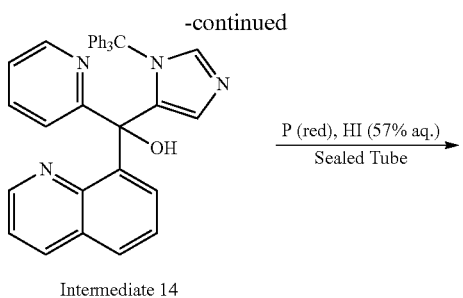

Intermediate 14

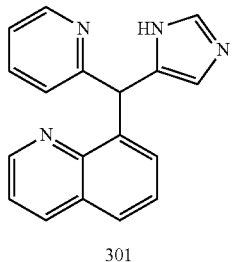

301

A solution of 4-iodo-1-tritylimidazole (commercially available) 5.2 g, 11.94 mmol) in dichloromethane (80 mL) at −10° C. was treated with ethyl magnesium bromide (3.98 mL, 11.94 mmol, 3M in ether) and allowed to react for 45 m. A solution of quinoline-8-carbaldehyde, (Intermediate 11) (1.5 g, 9.55 mmol) in dichloromethane was added via syringe at −10° C. and stirred for 16 h at room temperature. The mixture was quenched with water (50 mL) and a sat. solution of ammonium chloride (50 mL) and subjected to an aqueous work-up. The residue was purified by chromatography on silica gel with 3% $NH_3$-MeOH: $CH_2Cl_2$ to give to give quinolin-8-yl(1-trityl-1H-imidazol-5-yl)methanol, (Intermediate 12) as a solid, (3.7 g 82.7%).

A mixture of quinolin-8-yl(1-trityl-1H-imidazol-5-yl)methanol, (Intermediate 12) 3.7 g, 7.9 mmol) in $CH_2Cl_2$ (50 mL) was treated with manganese(IV) oxide, activated (commercially available from Aldrich): $MnO_2$ (4.1 g, 47.4 mmol) at room temperature. The mixture was heated to 60° C. for 2 h. The mixture was then cooled to room temperature and filtered through celite and the solvent was removed under vacuum to get quinolin-8-yl(1-trityl-1H-imidazol-5-yl)methanone, (Intermediate 13) (3.6 g, 97%).

A solution of 2-iodo-pyridine (commercially available) (307 mg, 1.5 mmol) in dichloromethane (20 mL) at room temperature was treated with ethyl magnesium bromide (0.50 mL, 1.5 mmol, 3M in ether) and allowed to react for 45 m. A solution quinolin-8-yl(1-trityl-1H-imidazol-5-yl)methanone, (Intermediate 13) (465 mg, 1.00 mmol) in dichloromethane was added via syringe at room temperature and the reaction mixture was then stirred at room temperature for 16 h. The mixture was quenched with water (20 mL) and a sat. solution of ammonium chloride (20 mL). The residue was isolated in a typical aqueous to give pyridin-2-yl(quinolin-8-yl)(1-trityl-1H-imidazol-5-yl)methanol, (Intermediate 14) (385 mg, crude).

A mixture of pyridin-2-yl(quinolin-8-yl)(1-trityl-1H-imidazol-5-yl)methanol (Intermediate 14) (385 mg, 0.70 mmol) in 57% aqueous HI (10 mL) and iPrOH (2 mL) was added red phosphorus (219 mg, 7.0 mmol) in a resealable tube was heated at 160° C. for 16 h. The mixture was then cooled to room temperature and poured into ice-water, which was then basified with NaOH and diluted with $CHCl_3$. The residue was isolated in a typical aqueous workup using $CHCl_3$ and purified by MPLC with 5 to 15% MeOH:$CH_2Cl_2$ to give 8-((1H-imidazol-5-yl)(pyridin-2-yl)methyl)quinoline, (658) as a solid, 236 mg (61% in two steps). $^1$HNMR ($CD_3OD$, 300 MHz) δ 8.82 (dd, J=1.8, 4.5 Hz, 1H), 8.43 (dd, J=1.8, 5.7 Hz, 1H), 8.28 (dd, J=1.8, 8.4 Hz, 1H), 7.83 (dd, J=4.0, 7.8 Hz, 1H), 7.73-7.70 (m, 2H), 7.68-7.43 (m, 3H), 7.25-7.21 (m, 2H), 7.03 (s, 1H), 6.52 (s, 1H).

Biological Data

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors. The $EC_{50}$ is the concentration at which the drug effect is half of its maximal effect.

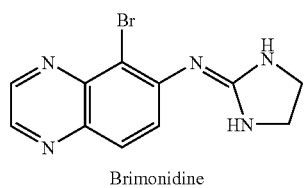 [SMILES: Brc1c(N=C2NCCN2)ccc2nccnc12]

Brimonidine

The results of the RSAT assay with several exemplary compounds of the invention are disclosed in Table 1 above together with the chemical formulas of these exemplary compounds. $EC_{50}$ values are nanomolar. ND stands for "not determinable" at concentrations less than 10 micromolar. IA stands for "intrinsic activity."

TABLE 1

Biological Data: Intrinsic Activity potency nM efficacy (EC50)

| Structure | Alpha 2A | Alpha 2B | Alpha 2C |
|---|---|---|---|
| 301 | ND (0.15) | 22 (1.00) | 275 (0.60) |
| 302 | 576 (0.50) | 2.15 (1.29) | 123 (1.16) |
| 116 | ND (0.13) | 348 (0.45) | ND (0.22) |
| 319 | ND (0.12) | 231 (0.90) | ND (0.33) |
| 320 | ND | 771 (0.65) | ND (0.18) |
| 315 | nd (0.23) | 9.12 (0.87) | 159 (0.86) |
| 316 | 430 (0.46) | 10 (1.13) | 157 (1.12) |

The following compounds have been synthesized by the method described above:

8-((1H-imidazol-5-yl)(pyridin-3-yl)methyl)quinoline, 302

$^1$H NMR (300 MHz, CDCl$_3$): δ 8.82 (dd, J=1.8, 4.5 Hz, 1H), 8.42 (d, J=2.1 Hz, 1H), 8.33 (dd, J=1.5, 4.8 Hz, 1H), 8.28 (dd, J=1.8, 8.1 Hz, 1H), 7.83 (dd, J=1.5, 8.1 Hz, 1H), 7.69 (d, J=1.2, Hz, 1H), 7.67-7.63 (m, 1H), 7.56-7.43 (m, 3H), 7.30 (dd, J=4.8, 8.1 Hz, 1H), 6.95 (s, 1H), 6.57 (s, 1H).

5-((1H-imidazol-5-yl)(pyridin-2-yl)methyl)quinoline, 116

$^1$H NMR (300 MHz, CDCl$_3$): δ 8.82 (dd, J=1.5, 4.2 Hz, 1H), 8.56 (d, J=8.7 Hz, 1H), 8.51-8.49 (m, 1H), 7.97 (d, J=8.7 Hz, 1H), 7.77-7.66 (m, 3H), 7.47 (dd, J=4.5, 8.7 Hz, 1H), 7.32-7.26 (m, 1H), 7.20 (t, J=8.1 Hz, 2H), 6.54 (s, 1H), 6.39 (s, 1H).

5-((1H-imidazol-4-yl)(pyridin-3-yl)methyl)quinoline, 319

$^1$H NMR (300 MHz, CDCl$_3$): δ 8.81 (dd, J=4.5, 1.8 Hz, 1H), 8.43 (d, J=2.1 Hz, 1H), 8.41 (dd, J=4.8, 1.8 Hz, 1H), 8.26 (d, J=8.7 Hz, 1H), 7.96 (d, J=8.7 Hz, 1H), 7.56 (dd, J=8.7, 7.5 Hz, 1H), 7.48 (s, 1H), 7.39 (dt, J=8.1, 1.8 Hz, 1H), 7.28 (dd, J=8.4, 3.9 Hz, 1H), 7.16 (dd, J=7.8, 5.1 Hz, 1H), 7.08 (d, J=6.9 Hz, 1H), 6.29 (s, 1H), 6.12 (s, 1H).

5-((1H-imidazol-4-yl)(pyridin-4-yl)methyl)quinoline, 320

$^1$H NMR (300 MHz, CDCl$_3$): δ 8.82 (dd, J=4.2, 1.5 Hz, 1H), 8.46-8.44 (m, 2H), 8.23 (d, J=8.4 Hz, 1H), 7.98 (d, J=8.4 Hz, 1H), 7.57 (dd, J=8.4, 7.2 Hz, 1H), 7.53 (s, 1H), 7.28 (dd, J=8.7, 4.5 Hz, 1H), 7.11-7.06 (m, 3H), 6.34 (s, 1H), 6.09 (s, 1H).

Methods of formulating these compounds are well known in the art. For example, U.S. Pat. No. 7,141,597 (especially column 10, line 27 to column 14, line 47) contains information that may be used for general guidance. Similar relevant information is also available in numerous other sources. The biological activity of the compounds disclosed herein (e.g. Table 1) may be used for additional general guidance on dosage, depending on the particular use of a compound.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound of the formula

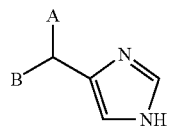

wherein A is monocyclic heteroaryl having 0, 1, 2, or 3 substituents; and B is a fused ring system consisting of:
 a. a phenyl ring, wherein there is a single covalent bond between a carbon atom of the phenyl ring and the carbon atom attached to A and the imidazolyl ring;
 b. a second heterocyclic six-membered ring which is fused to the phenyl ring, and
 c. 0, 1, 2, or 3 substituents which attach to one or both of the phenyl ring and the second ring;

wherein each substituent independently consists of from 0 to 8 carbon atoms, from 0 to 3 oxygen atoms, from 0 to 3 halogen atoms, from 0 to 2 nitrogen atoms, from 0 to 2 sulfur atoms, and from 0 to 24 hydrogen atoms.

2. The compound of claim 1 wherein A is pyridinyl, thienyl, furyl, or pyrrolyl.

3. The compound of claim 2 wherein B is quinolinyl, indolyl, benzothienyl, benzofuryl, benzofuranyl, benzodioxolyl, or 2,3-dihydrobenzo[b][1,4]dioxin-6-yl.

4. The compound of claim 3 wherein each substituent is independently —H, alkyl having from 1 to 8 carbon atoms, —F, —Cl, —Br, —CH$_2$OH, an amine having from 0 to 8 carbon atoms, —CH$_2$CN, —CF$_3$, or acyl having from 1 to 8 carbons.

5. The compound of claim 4 wherein A is pyridinyl.

6. The compound of claim 5 wherein B is quinolinyl.

7. The compound of claim 6 wherein each substituent of B is —H, —F, —Cl, —Br, —CH$_3$, —NHCH$_3$, or —CF$_3$.

8. The compound of claim 7 having the formula

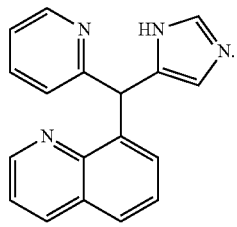 [SMILES: c1ccc(C(c2cnc[nH]2)c2cccc3cccnc23)nc1]

9. The compound of claim 7 having the formula

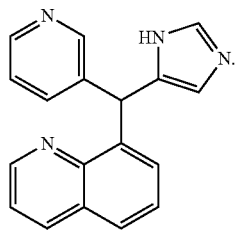 [SMILES: c1cncc(C(c2cnc[nH]2)c2cccc3cccnc23)c1]

10. The compound of claim 7 having the formula

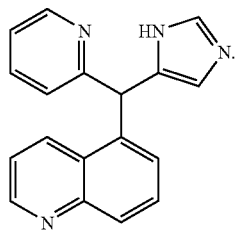 [SMILES: c1ccc(C(c2cnc[nH]2)c2cccc3ncccc23)nc1]

11. The compound of claim 7 having the formula

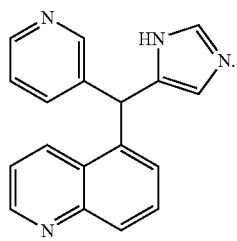 [SMILES: c1cncc(C(c2cnc[nH]2)c2cccc3ncccc23)c1]

12. The compound of claim 7 having the formula

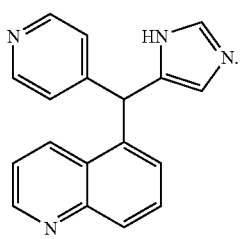 [SMILES: c1cc(C(c2ccncc2)c2cnc[nH]2)c2cccnc2c1]

13. A method of treating pain comprising administering a compound according to claim 1 to a mammal in need thereof.

14. The method of claim 13 wherein the pain is chronic pain.

15. The method of claim 14 wherein the pain is chronic neuropathic pain or visceral pain.

16. A dosage form comprising a compound according to claim 1.

* * * * *